United States Patent

Kaufmann et al.

[11] Patent Number: 5,770,752
[45] Date of Patent: Jun. 23, 1998

[54] PROCESS FOR REDUCING THE CONCENTRATION OF BY-PRODUCTS IN PRODUCT MIXTURES

[75] Inventors: Wilhelm Kaufmann, Rödermark; Thomas Wisser, Limburg; Johann Streb, Frankfurt; Thomas Rink; Roland Zenk, both of Bad Soden; Michael Riedel, Essen; Ivan Cabrera, Dreieich, all of Germany

[73] Assignee: Targor GmbH, Ludwigshafen, Germany

[21] Appl. No.: 768,638

[22] Filed: Dec. 18, 1996

[30] Foreign Application Priority Data

Dec. 18, 1995 [DE] Germany ............ 195 47 247.0
Dec. 18, 1995 [DE] Germany ............ 195 47 248.9

[51] Int. Cl.⁶ .................. C07F 17/00; C07F 7/02
[52] U.S. Cl. .............. 556/11; 556/12; 556/43; 556/47; 556/53; 526/160; 526/943; 502/103
[58] Field of Search .................. 556/11, 12, 43, 556/47, 53; 526/443, 160, 943

[56] References Cited

U.S. PATENT DOCUMENTS

| | | | |
|---|---|---|---|
| 4,752,597 | 6/1988 | Turner | 502/104 |
| 5,017,714 | 5/1991 | Welborn, Jr. | 556/12 |
| 5,103,030 | 4/1992 | Rohrmann et al. | 556/12 |
| 5,278,264 | 1/1994 | Spaleck et al. | 526/127 |
| 5,324,800 | 6/1994 | Welborn, Jr. et al. | 526/160 |
| 5,455,366 | 10/1995 | Rohrmann et al. | 556/8 |
| 5,556,997 | 9/1996 | Strickler et al. | 556/11 |

FOREIGN PATENT DOCUMENTS

| | | |
|---|---|---|
| 2 011 879 | 9/1990 | Canada . |
| 1 319 784 | 6/1993 | Canada . |
| 0 129 368 | 12/1984 | European Pat. Off. . |
| 0 336 128 | 10/1989 | European Pat. Off. . |
| 0 387 690 | 9/1990 | European Pat. Off. . |
| 0 530 647 | 3/1993 | European Pat. Off. . |
| 0 537 686 | 4/1993 | European Pat. Off. . |
| 0 549 900 | 7/1993 | European Pat. Off. . |

OTHER PUBLICATIONS

Hans–Herbert Brintzinger et al, "Stereospezifische Olefinpolymerisation mit chirlan Metallcocenkatalysatoren", Angew. Chem., 1995, 107, pp. 1255–1283.

Hans H. Brintzinger et al, "Stereospecific Olefin Polymerization with Chiral Metallocene Catalysts", Angew. Chem. Int. Ed. Engl., 34 (1995) pp. 1143–1170.

H. G. Alt et al, "Verbruckte Bis(fluorenyl)komplexe des Zirconiums und Hafniums . . . ", J. Organomet. Chem., 472 (1994), pp. 113–118.

*Primary Examiner*—Porfirio Nazario-Gonzalez
*Attorney, Agent, or Firm*—Connolly & Hutz

[57] ABSTRACT

The present invention relates to a process for reducing the concentration of organometallic and/or inorganic by-products in product mixtures formed in the synthesis of metallocenes, which comprises treating a mixture comprising one or more metallocenes and one or more organometallic and/or inorganic by-products with a polar extractant.

12 Claims, No Drawings

PROCESS FOR REDUCING THE CONCENTRATION OF BY-PRODUCTS IN PRODUCT MIXTURES

The present invention relates to a process for reducing the concentration of organometallic and/or inorganic by-products in product mixtures formed in the synthesis of metallocenes, in particular for separating off isomeric metallocenes and/or metal halides which are formed in the metallocene synthesis.

Metallocenes can, if desired in combination with one or more cocatalysts, be used as catalysts for the polymerization and copolymerization of olefins. In particular, the catalysts are produced from halogen-containing metallocene complexes which can be converted, for example by means of an aluminoxane, into a polymerization-active cationic metallocene complex (EP-A-129368).

The synthesis of metallocenes is known (U.S. Pat. No. 4752597; U.S. Pat. No. 5017714; U.S. Pat. No. 5103030; EP-A-336128; EP-A-387690; EP-A-530647; EP-A-537686; EP-A-549900; H. -H. Brintzinger, D. Fischer, R. M ülhaupt, B. Rieger and R. Waymouth, Angew. Chem., 107 (1995) 1255; Angew. Chem. Int. Ed. Engl., 34 (1995) 1143; M. Aulbach and F. Küber, ChiuZ, 28 (1994) 197). For this purpose, metal compounds such as metal alkoxides or metal halides, e.g. $TiCl_4$, $ZrCl_4$, $HfCl_4$, can be reacted with a wide variety of cyclopentadienyl-metal compounds. This reaction produces considerable amounts of inorganic by-products (e.g. salts) which are mixed with the metallocene. When metallocenes are used as catalysts for olefin polymerization, these inorganic by-products impair the catalyst activity. To apply metallocene catalysts to a support, the metallocenes are generally activated with a cocatalyst and applied as solution in a nonpolar solvent to a solid support. Here too, a low content of inorganic by-products in the metallocene used is advantageous.

The separation of metallocene and inorganic by-products is customarily carried out by dissolving the metallocene in organic solvents, with the inorganic by-products being able to be removed as sparingly soluble components. Toluene and dichloromethane are used particularly frequently as solvents, but other solvents such as tetrahydrofuran, diethyl ether, aliphatic, aromatic and chlorinated hydrocarbons are also used. Disadvantages of this method are that many metallocenes are only moderately soluble in the customary organic solvents and therefore large amounts of solvent, large filtration apparatuses and a great amount of time are required. In addition, large amounts of toxic or environmentally unfriendly solvents are often used. Since the inorganic by-products are often obtained in very finely divided form, filtration times can become very long even when filter aids are added and filtration is carried out under pressure. To be able to isolate the metallocene as completely as possible from the filtrate, the solvent generally has to be distilled off. This raises the problem of such metallocene solutions having limited stability toward impurities such as bases, protic compounds and traces of moisture as well as toward heat.

Furthermore, the synthesis of metallocenes can result in formation of considerable amounts of organometallic by-products (e.g. isomers) which are mixed with the desired metallocene and can impair its catalytic properties. For example, the bridged bisindenyl metallocenes which are particularly attractive for olefin polymerization are generally formed as a mixture of racemic and meso forms. However, often only one of these isomeric compounds is suitable for the stereoselective polymerization of olefins (e.g. the racemate) while the other isomer (in the case of the bridged bisindenyl metallocenes this is usually the meso form) frequently has a lower stereoselectivity and is separated off.

The isolation of a desired metallocene can be carried out by completely dissolving the crude product obtained in the synthesis in a suitable solvent (H. G. Alt et al., J. Organomet. Chem., 472 (1994) p. 113), with the concentration of undesired organometallic by-products (e.g. isomers) being reduced by subsequent fractional crystallization or fractional precipitation. Since many metallocenes are only moderately soluble in the customary solvents, the complete dissolution of the crude product requires large amounts of solvent, large filtration apparatuses and a great amount of time. This procedure is associated with sometimes considerable yield losses if relatively high purities of certain metallocenes are sought. In addition, large amounts of toxic or environmentally unfriendly solvents are often used for the complete dissolution. Furthermore, many metallocenes in dissolved form are sensitive toward impurities such as bases, protic compounds and traces of moisture as well as toward heat.

It is thus an object of the invention to provide a simple, gentle and effective process for reducing the concentration of organometallic and/or inorganic by-products formed in the synthesis of metallocenes.

The present invention accordingly provides a process for reducing the concentration of organometallic and/or inorganic by-products in product mixtures formed in the synthesis of metallocenes, which comprises treating a mixture comprising one or more metallocenes and one or more organometallic and/or inorganic by-products with a polar extractant.

The mixture treated in the process of the invention is preferably the crude product formed directly in the metallocene synthesis. However, the crude product can also be pretreated, e.g. with solvents.

For the purposes of the present invention, the term "inorganic by-product" refers to, for example, inorganic salts or covalent metal halides (e.g. fluorides, chlorides, bromides or iodides). The inorganic salts have, for example, the formula (I)

$$M^2X^2_o \qquad\qquad (I),$$

where $M^2$ is a metal of main group I, II or III of the Periodic Table of the Elements, Zn or Cd, preferably Li, Na, K, Mg or Ca, particularly preferably Li or Na, $X^2$ are identical or different and are each a halogen atom such as fluorine, chlorine, bromine or iodine, preferably chlorine, bromine or iodine, particularly preferably chlorine, and o corresponds to the valence of $M^2$ and is 1, 2 or 3.

Examples of salts of the formula (I) are LiF, LiCl, LiBr, LiI, NaF, NaCl, NaBr, NaI, KF, KCl, KBr, KI, $CaF_2$, $CaCl_2$, $CaBr_2$, $CaI_2$, CsF, CsCl, CsBr, CsI, $MgF_2$, $MgCl_2$, MgBrCl, $BaCl_2$, $BaI_2$, $AlF_3$, $AlCl_3$, $AlBrCl_2$, $ZnCl_2$, $ZnBr_2$, $CdCl_2$, CdBrI.

Examples of covalent metal halides are halides of metals of transition group III, IV, V or VI, in particular IV, of the Periodic Table of the Elements, e.g. $TiCl_4$, $ZrCl_4$ or $HfCl_4$.

The term "inorganic by-product" is also used when the desired metallocene makes up only a small part (for instance less than 50% by weight) of the mixture and one or more of the constituents referred to as "inorganic by-products" are present in predominant amounts.

For the purposes of the present invention, the term "organometallic by-product" refers to all organometallic compounds which contain the same metal as the desired metallocene; at least one carbon-containing ligand, in particular a π-ligand such as a cyclopentadienyl ligand, is bonded to this metal. This definition excludes the desired metallocene itself which is to be purified or upgraded.

Examples of compounds covered by the term "organometallic by-product" are those metallocenes which are isomers of the desired metallocene, other metallocenes which are not isomeric with the desired metallocene, organometallic compounds which are formed or remain in the metallocene synthesis as a result of incomplete reaction (e.g. metall alkyl compounds such as butyllithium or Grignard reagents), oligomeric and polymeric reaction products and also compounds formed from the desired metallocene or one of the abovementioned by-products by reaction with impurities such as water, alcohols, amines, basic compounds, air or by thermal decomposition. The term "organometallic by-product" is also used when the desired metallocene makes up only a small part (for instance less than 50 per cent by weight) of the mixture and one or more of the constituents referred to as "organometallic by-products" are present in predominant amounts.

The metallocene(s) present in the mixture comprise at least one central metal atom to which are bound at least two π-ligands, e.g. cyclopentadienyl ligands. In addition, further substituents such as halogen, alkyl, alkoxy or aryl can be bound to the central metal atom. The central metal atom is preferably an element of transition group III, IV, V or VI of the Periodic Table of the Elements, in particular of transition group IV of the Periodic Table of the Elements, e.g. Zr or Hf. For the purposes of the present invention, cyclopentadienyl ligands are unsubstituted cyclopentadienyl radicals or substituted cyclopentadienyl radicals such as methylcyclopentadienyl, indenyl, 2-methylindenyl, tetrahydroindenyl, benzoindenyl, fluorenyl, benzofluorenyl, tetrahydrofluorenyl, octahydrofluorenyl. The π-ligands, e.g. cyclopentadienyl ligands, can be unbridged or bridged, with single and multiple bridges, also via ring systems, being possible. The term metallocene also includes compounds having more than one metallocene fragment, known as multinuclear metallocenes. These can have any substitution pattern and bridging variants. The individual metallocene fragments of such multinuclear metallocenes can be either of the same type or different from one another. Examples of such multinuclear metallocenes are described, for example, in EP-A-632063, JP-A-04/80214, JP-A-04/85310, EP-A-654476.

Preference is given to unbridged or bridged metallocenes of the formula II,

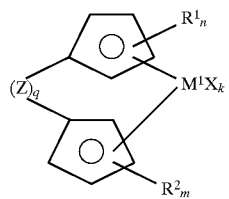

(II)

where $M^1$ is a metal of transition group III., IV., V. or VI. of the Periodic Table of the Elements, in particular Zr or Hf, $R^1$ are identical or different and are each a hydrogen atom, $SiR^3{}_3$ where $R^3$ are identical or different and are each a hydrogen atom or a $C_1$–$C_{40}$-group such as $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^1$ are a $C_1$–$C_{30}$-group such as $C_1$–$C_{25}$-alkyl, e.g. methyl, ethyl, t-butyl, cyclohexyl or octyl, fluorine-containing $C_1$–$C_{25}$-alkyl, $C_2$–$C_{25}$-alkenyl, $C_3$–$C_{15}$-alkylalkenyl, $C_6$–$C_{24}$-aryl, $C_5$–$C_{24}$-heteroaryl such as pyridyl, furyl or quinolyl, $C_7$–$C_{30}$-arylalkyl, $C_7$–$C_{30}$-alkylaryl, fluorine-containing $C_6$–$C_{24}$-aryl, fluorine-containing $C_7$–$C_{30}$-arylalkyl, fluorine-containing $C_7$–$C_{30}$-alkylaryl, $C_1$–$C_{12}$-alkoxy, or two or more radicals $R^1$ can be connected cyclically to one another in such a way that the radicals $R^1$ and the atoms of the cyclopentadienyl ring which connect them form a $C_4$–$C_{24}$-ring system which may in turn be substituted, $R^2$ are identical or different and are each a hydrogen atom, $SiR^3{}_3$, where $R^3$ are identical or different and are each a hydrogen atom or a $C_1$–$C_{40}$-group such as $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^2$ are a $C_1$–$C_{30}$-group such as $C_1$–$C_{25}$-alkyl, e.g. methyl, ethyl, tert-butyl, cyclohexyl or octyl, fluorine-containing $C_1$–$C_{25}$-alkyl, $C_2$–$C_{25}$-alkenyl, $C_3$–$C_{15}$-alkylalkenyl, $C_6$–$C_{24}$-aryl, $C_5$–$C_{24}$-heteroaryl, e.g. pyridyl, furyl or quinolyl, $C_7$–$C_{30}$-arylalkyl, $C_7$–$C_{30}$-alkylaryl, fluorine-containing $C_6$–$C_{24}$-aryl, fluorine-containing $C_7$–$C_{30}$-arylalkyl, fluorine-containing $C_7$–$C_{30}$-alkylaryl or $C_1$–$C_{12}$-alkoxy, or two or more radicals $R^2$ can be cyclically connected to one another in such a way that the radicals $R^2$ and the atoms of the cyclopentadienyl ring which connect them form a $C_4$–$C_{24}$-ring system which may in turn be substituted, n is 5 for q=0, and n is 4 for q=1, m is 5 for q=0, and m is 4 for q=1, X are identical or different and are each a halogen atom or a hydrocarbon radical having 1–20 carbon atoms, e.g. $C_1$–$C_{20}$-alkyl, $C_1$–$C_{20}$-alkoxy or $C_6$–$C_{14}$-aryloxy, k is an integer from 1 to 4 and is preferably 2 when $M^1$=Ti, Zr or Hf, Z is a structural bridge between the two cyclopentadienyl rings, and q is 0 or 1.

Examples of Z are groups $(M^2R^4R^5)_y$, where $M^2$ is carbon, silicon, germanium or tin and $R^4$ and $R^5$ are identical or different and are each a $C_1$–$C_{20}$-hydrocarbon group such as $C_1$–$C_{10}$-alkyl or $C_6$–$C_{14}$-aryl and y is 1 or 2. Z is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)_2Si$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$. Z can also form, together with one or more radicals $R^1$ and/or $R^2$, a monocyclic or polycyclic ring system.

Particular preference is given to chiral bridged metallocenes of the formula II, in particular those in which q is 1 and one or both cyclopentadienyl rings are substituted such that they form an indenyl ring. The indenyl ring is preferably substituted, in particular in the 2 position, the 2,4 positions, 2,4,5 positions, 2,4,6 positions, 2,4,7 positions or 2,4,5,6 positions, by $C_1$–$C_{20}$-groups such as $C_1$–$C_{10}$-alkyl or $C_6$–$C_{20}$-aryl, where two or more substituents can also form a ring system.

The following examples of metallocenes illustrate the invention but do not restrict it in any way:
bis(cyclopentadienyl)zirconium dichloride
bis(indenyl)zirconium dichloride
bis(fluorenyl)zirconium dichloride
(indenyl)(fluorenyl)zirconium dichloride
(3-methyl-5-naphthylindenyl)(2,7-di-tert-butylfluorenyl) zirconium dichloride (3-methyl-5-naphthylindenyl)(3,4,7-trimethoxyfluorenyl) zirconium dichloride
(pentamethylcyclopentadienyl)(tetrahydroindenyl) zirconium dichloride
(cyclopentadienyl)(1-octen-8-ylcyclopentadienyl)zirconium dichloride
(indenyl)(1-buten-4-ylcyclopentadienyl)zirconium dichloride
[1,3-bis(trimethylsilyl)cyclopentadienyl](3,4-benzofluorenyl)zirconium dichloride
bis(cyclopentadienyl)titanium dichloride
dimethylsilanediylbis(indenyl)zirconium dichloride
dimethylsilanediylbis(tetrahydroindenyl)zirconium dichloride
dimethylsilanediyl(cyclopentadienyl)(indenyl)zirconium dichloride
dimethylsilanediylbis(2-methylindenyl)zirconium dichloride
dimethylsilanediylbis(2-ethylindenyl)zirconium dichloride
dimethylsilanediylbis(2-methyl-4,5-benzoindenyl) zirconium dichloride
dimethylsilanediylbis(2-ethyl-4,5-benzoindenyl)zirconium dichloride
dimethylsilanediylbis(4, 5-dihydro-8-methyl-7H-cyclopent[e]acenaphthylen-7-yliden]zirconium dichloride
dimethylsilanediyl(2-methyl-4,5-benzoindenyl)(2-methyl-4-phenylindenyl)zirconium dichloride
dimethylsilanediyl(2-ethyl-4,5-benzoindenyl)(2-methyl-4-phenylindenyl)zirconium dichloride
dimethylsilanediyl(2-methyl-4,5-benzoindenyl)(2-ethyl-4-phenylindenyl)zirconium dichloride
dimethylsilanediyl(2-ethyl-4,5-benzoindenyl)(2-ethyl-4-naphthylindenyl)zirconium dichloride
dimethylsilanediyl(2-methylindenyl)(4-phenylindenyl) zirconium dichloride
dimethylsilanediylbis(2-methyl4-phenylindenyl)zirconium dichloride
dimethylsilanediylbis(2-ethyl4-phenylindenyl)zirconium dichloride
dimethylsilanediylbis(2-methyl-4,6-diisopropylindenyl) zirconium dichloride
dimethylsilanediylbis(2-ethyl-4,6-diisopropylindenyl) zirconium dichloride
dimethylsilanediylbis(2-methyl-4-naphthylindenyl) zirconium dichloride
dimethylsilanediylbis(2-ethyl-4-naphthylindenyl)zirconium dichloride
methylphenylsilanediylbis(indenyl)zirconium dichloride
methylphenylsilanediyl(cyclopentadienyl)(indenyl) zirconium dichloride
methylphenylsilanediylbis(tetrahydroindenyl )zirconium dichloride
methylphenylsilanediylbis(2-methylindenyl)zirconium dichloride
methylphenylsilanediylbis(2-ethylindenyl)zirconium dichloride
methylphenylsilanediylbis(2-methyl-4,5-benzoindenyl) zirconium dichloride
methylphenylsilanediylbis(2-ethyl-4,5-benzoindenyl) zirconium dichloride
methylphenylsilanediylbis(4,5-dihydro-8-methyl-7H-cyclopent[e]acenaphthylen-7-ylidene]zirconium dichloride
methylphenylsilanediyl(2-methyl-4,5-benzoindenyl)(2-methyl-4-phenylindenyl)zirconium dichloride
methylphenylsilanediyl(2-ethyl4,5-benzoindenyl)(2-methyl-4-phenylindenyl)zirconium dichloride
methylphenylsilanediyl(2-methyl-4,5-benzoindenyl)(2-ethyl-4-phenylindenyl)zirconium dichloride
methylphenylsilanediyl(2-ethyl-4, 5-benzoindenyl)(2-ethyl-4-naphthylindenyl)zirconium dichloride
methyiphenylsilanediyl(2-methylindenyl)(4-phenylindenyl) zirconium dichloride
methylphenylsilanediylbis(2-methyl-4-phenylindenyl) zirconium dichloride
methylphenylsilanediylbis(2-ethyl-4-phenylindenyl) zirconium dichloride
methylphenylsilanediylbis(2-methyl-4,6-diisopropylindenyl)zirconium dichloride
methylphenylsilanediylbis(2-ethyl-4,6-diisopropylindenyl) zirconium dichloride
methylphenylsilanediylbis(2-methyl-4-naphthylindenyl) zirconium dichloride
methylphenylsilanediylbis(2-ethyl-4-naphthylindenyl) zirconium dichloride
diphenylsilanediylbis(indenyl)zirconium dichloride
diphenylsilanediylbis(2-methylindenyl)zirconium dichloride
diphenylsilanediylbis(2-ethylindenyl)zirconium dichloride
diphenylsilanediyl(cyclopentadienyl)(indenyl)zirconium dichloride
diphenylsilanediylbis(2-methyl4,5-benzoindenyl)zirconium dichloride
diphenylsilanediylbis(2-ethyl-4,5-benzoindenyl)zirconium dichloride
diphenylsilanediyl(2-methyl-4, 5-benzoindenyl)(2-methyl-4-phenylindenyl)zirconium dichloride
diphenylsilanediyl(2-ethyl-4,5-benzoindenyl)(2-methyl-4-phenylindenyl)zirconium dichloride
diphenylsilanediyl(2-methyl-4, 5-benzoindenyl )(2-ethyl-4-phenylindenyl )zirconium dichloride
diphenylsilanediyl(2-ethyl-4, 5-benzoindenyl )(2-ethyl-4-naphthylindenyl)zirconium dichloride
diphenylsilanediyl(2-methyl indenyl)(4-phenyl indenyl) zirconium dichloride
diphenylsilanediylbis(2-methyl-4-phenylindenyl)zirconium dichloride
diphenylsilanediylbis(2-ethyl-4-phenylindenyl)zirconium dichloride
diphenylsilanediylbis(2-methyl-4,6-diisopropylindenyl) zirconium dichloride
diphenylsilanediylbis(2-ethyl-4,6-diisopropylindenyl) zirconium dichloride
diphenylsilanediylbis(2-methyl-4-naphthylindenyl) zirconium dichloride
diphenylsilanediylbis(2-ethyl-4-naphthylindenyl)zirconium dichloride
1-silacyclopentane-1,1-bis(indenyl)zirconium dichloride
1-silacyclopentane-1,1 -bis(2-methylindenyl)zirconium dichloride
1-silacyclopentane-1,1-bis(2-ethylindenyl)zirconium dichloride
1-silacyclopentane-1,1-bis(2-methyl-4,5-benzoindenyl) zirconium dichloride
1-silacyclopentane-1-bis(2-ethyl-4,5-benzoindenyl) zirconium dichloride
1-silacyclopentane-1-(2-methyl-4,5-benzoindenyl)-1-(2-methyl4-phenylindenyl)zirconium dichloride
1-silacyclopentane-1-(2-ethyl-4,5-benzoindenyl)-1-(2-methyl-4-phenylindenyl)zirconium dichloride
1-silacyclopentane-1-(2-methyl-4,5-benzoindenyl)-1-(2-ethyl-4-phenylindenyl)zirconium dichloride
1-silacyclopentane-1-(2-ethyl-4,5-benzoindenyl)-1-(2-ethyl-4-naphthylindenyl)zirconium dichloride 1-silacyclopentane-1-(2-methylindenyl)-1-(4-phenylindenyl)zirconium dichloride
1-silacyclopentane-1,1-bis(2-methyl-4-phenylindenyl)zirconium dichloride
1-silacyclopentane-1,1-bis(2-ethyl-4-phenylindenyl)zirconium dichloride
1-silacyclopentane-1,1-bis(2-methyl-4,6-diisopropylindenyl)zirconium dichloride
1-silacyclopentane-1,1-bis(2-ethyl-4,6-diisopropylindenyl)zirconium dichloride
1-silacyclopentane-1,1-bis(2-methyl-4-naphthylindenyl)zirconium dichloride
1-silacyclopentane-1,1-bis(2-ethyl-4-naphthylindenyl)zirconium dichloride bis(cyclopentadienyl)titanium dichloride
ethylene-1,2-bis(indenyl)zirconium dichloride
ethylene-1,2-bis(tetrahydroindenyl)zirconium dichloride
ethylene-1-cyclopentadienyl-2-(1-indenyl)zirconium dichloride
ethylene-1-cyclopentadienyl-2-(2-indenyl)zirconium dichloride
ethylene-1-cyclopentadienyl-2-(2-methyl-1-indenyl)zirconium dichloride
ethylene-1,2-bis(2-methylindenyl)zirconium dichloride
ethylene-1,2-bis(2-ethylindenyl)zirconium dichloride
ethylene-1,2-bis(2-methyl-4,5-benzoindenyl)zirconium dichloride
ethylene-1,2-bis(2-ethyl-4,5-benzoindenyl)zirconium dichloride
ethylene-1,2-bis(4,5-dihydro-8-methyl-7H-cyclopent[e]acenaphthylen-7-ylidene]zirconium dichloride
ethylene-1-(2-methyl-4,5-benzoindenyl)-2-(2-methyl-4-phenylindenyl)zirconium dichloride
ethylene-1-(2-ethyl-4,5-benzoindenyl)-2-(2-methyl-4-phenylindenyl)zirconium dichloride
ethylene-1-(2-methyl4,5-benzoindenyl)-2-(2-ethyl-4-phenylindenyl)zirconium dichloride
ethylene-1-(2-ethyl-4,5-benzoindenyl)-2-(2-ethyl-4-naphthylindenyl)zirconium dichloride
ethylene-1-(2-methylindenyl)-2-(4-phenylindenyl)zirconium dichloride
ethylene-1,2-bis(2-methyl-4-phenylindenyl)zirconium dichloride
ethylene-1,2-bis(2-ethyl-4-phenylindenyl)zirconium dichloride
ethylene-1,2-bis(2-methyl-4,6-diisopropylindenyl)zirconium dichloride
ethylene-1,2-bis(2-ethyl-4,6-diisopropylindenyl)zirconium dichloride
ethylene-1,2-bis(2-methyl-4-naphthylindenyl)zirconium dichloride
ethylene-1,2-bis(2-ethyl-4-naphthylindenyl)zirconium dichloride
propylene-2,2-bis(indenyl)zirconium dichloride
propylene-2-cyclopentadienyl-2-(1-indenyl)zirconium dichloride
propylene-2-cyclopentadienyl-2-(4-phenyl-1-indenyl)zirconium dichloride
propylene-2-cyclopentadienyl-2-(9-fluorenyl)zirconium dichloride
propylene-2-cyclopentadienyl-2-(2,7-dimethoxy-9-fluorenyl)zirconium dichloride
propylene-2-cyclopentadienyl-2-(2,7-di-tert-butyl-9-fluorenyl)zirconium dichloride
propylene-2-cyclopentadienyl-2-(2,7-dibromo-9-fluorenyl)zirconium dichloride
propylene-2-cyclopentadienyl-2-(2,7-diphenyl-9-fluorenyl)zirconium dichloride
propylene-2-cyclopentadienyl-2-(2,7-dimethyl-9-fluorenyl)zirconium dichloride
propylene-2-(3-methylcyclopentadienyl)-2-(2,7-dibutyl-9-fluorenyl)zirconium dichloride
propylene-2-(3-tert-butylcyclopentadienyl)-2-(2,7-dibutyl-9-fluorenyl)zirconium dichloride
propylene-2-(3-trimethylsilylcyclopentadienyl)-2-(3,6-di-tert-butyl-9-fluorenyl)zirconium dichloride
propylene-2-cyclopentadienyl(-2-[2,7-bis(3-buten-1-yl)-9-fluorenyl]zirconium dichloride
propylene-2-cyclopentadienyl-2-(3-tert-butyl-9-fluorenyl)zirconium dichloride
propylene-2,2-bis(tetrahydroindenyl)zirconium dichloride
propylene-2,2-bis(2-methylindenyl)zirconium dichloride
propylene-2,2-bis(2-ethylindenyl)zirconium dichloride
propylene-2,2-bis(2-methyl4,5-benzoindenyl)zirconium dichloride
propylene-2,2-bis(2-ethyl-4,5-benzoindenyl)zirconium dichloride
propylene-2,2-bis(4,5-dihydro-8-methyl-7H-cyclopent[e]acenaphthylen-7-ylidene]zirconium dichloride
propylene-2-(2-methyl4,5-benzoindenyl)-2-(2-methyl-4-phenylindenyl)zirconium dichloride
propylene-2-(2-ethyl-4,5-benzoindenyl)-2-(2-methyl-4-phenylindenyl)zirconium dichloride
propylene-2-(2-methyl-4,5-benzoindenyl)-2-(2-ethyl4-phenylindenyl)zirconium dichloride
propylene-2-(2-ethyl-4,5-benzoindenyl)-2-(2-ethyl-4-naphthyl indenyl)zirconium dichloride
propylene-2-(2-methylindenyl)-2-(4-phenylindenyl)zirconium dichloride
propylene-2,2-bis(2-methyl-4-phenylindenyl)zirconium dichloride
propylene-2,2-bis(2-ethyl-4-phenyl indenyl )zirconium dichloride
propylene-2,2-bis(2-methyl-4,6-diisopropylindenyl)zirconium dichloride
propylene-2,2-bis(2-ethyl4,6-diisopropylindenyl)zirconium dichloride
propylene-2,2-bis(2-methyl4-naphthylindenyl)zirconium dichloride
propylene-2,2-bis(2-ethyl-4-naphthylindenyl)zirconium dichloride
1,6-bis[methylsilylbis(2-methyl-4-phenylindenyl)zirconium dichloride]hexane
1,6-bis[methylsilylbis(2-methyl-4,5-benzoindenyl)zirconium dichloride]hexane
1,6-bis[methylsilylbis(2-ethyl-4-phenylindenyl)zirconium dichloride]hexane
1,6-bis[(methylsilylbis(2-methyl-4-naphthylindenyl)zirconium dichloride]hexane
1,6-bis[methylsilylbis(2-methyl-4,6-diisopropylindenyl)zirconium dichloride]hexane
1,6-bis[methylsilyl(2-methyl-4-phenylindenyl)(4,5-benzoindenyl)zirconium dichloride]hexane
1-[methylsilylbis(tetrahydroindenyl)zirconium dichloride]-6-[ethylstannyl(cyclopentadienyl)-(fluorenyl)zirconium dichloride]hexane
1,6-disila-1,1,6,6-tetramethyl-1,6-bis[methylsilylbis(2-methyl-4-phenylindenyl)zirconium dichloride]hexane
1,4-disila-1,4-bis[methylsilylbis(2-methyl-4-phenylindenyl)zirconium dichloride)cyclohexane
[1,4-bis(1-indenyl)-1,1,4,4-tetramethyl-1,4-disilabutane]bis(pentamethylcyclopentadienylzirconium dichloride)
[1,4-bis(9-fluorenyl)-1,1,4,4-tetramethyl-1,4-disilabutane]bis(cyclopentadienylzirconium dichloride)
[1,4-bis(1-indenyl)-1,1,4,4-tetramethyl-1,4-disilabutane]bis(cyclopentadienylzirconium dichloride)

[1-(1-indenyl)-6-(2-phenyl-1-indenyl)-1,1,6,6-tetraethyl-1,6-disila-4-oxahexane]bis(tert-butylcyclopentadienylzirconium dichloride)
[1,10-bis(2,3-dimethyl-1-indenyl)-1,1,10,10-tetramethyl-1,10-digermadecane]bis(2-methyl-4-phenylindenylzirconium dichloride)
(1-methyl-3-tert-butylcyclopentadienyl)(1-phenyl-4-methoxy-7-chlorofluorenyl)zirconium dichloride
(4,7-dichloroindenyl)(3,6-dimesitylfluorenyl)zirconium dichloride bis(2,7-di-tert-butyl-9-cyclohexylfluorenyl)zirconium dichloride
(2,7-dimesitylfluorenyl)[2,7-bis(1-naphthyl)fluorenyl]zirconium dichloride
dimethylsilylbis(fluorenyl)zirconium dichloride
dibutylstannylbis(2-methylfluorenyl)zirconium dichloride
1,1,2,2-tetraethyldisilanediyl(2-methylindenyl)(4-phenylfluorenyl)zirconium dichloride
propylene-1-(2-indenyl)-2-(9-fluorenyl)zirconium dichloride
1,1-dimethyl-1-silaethylenebis(fluorenyl)zirconium dichloride
[4-(cyclopentadienyl )4,7,7-trimethyl(tetrahydroindenyl)]zirconium dichloride
[4-(cyclopentadienyl)-4,7-dimethyl-7-phenyl(5,6-dimethyltetrahydroindenyl)]zirconium dichloride
[4-(cyclopentadienyl)-4,7-dimethyl-7-(1-naphthyl)(7-phenyltetrahydroindenyl)]zirconium dichloride
[4-(cyclopentadienyl)-4,7-dimethyl-7-butyl(6,6-diethyltetrahydroindenyl)]zirconium dichloride
[4-(3-tert-butylcyclopentadienyl)-4,7,7-trimethyl(tetrahydroindenyl)]zirconium dichloride
[4-(1 -indenyl)-4,7,7-trimethyl(tetrahydroindenyl)]zirconium dichloride bis(cyclopentadienyl)hafnium dibromide
bis(indenyl)vanadium diiodide
bis(fluorenyl)scandium chloride
(indenyl)(fluorenyl)niobium diiodide
(2-methyl-7-naphthylindenyl)(2,6-di-tert-butylfluorenyl)titanium dichloride
(pentamethylcyclopentadienyl)(tetrahydroindenyl)hafnium bromide chloride
(cyclopentadienyl)(1-octen-8-ylcyclopentadienyl)hafnium dichloride
(indenyl)(2-buten-4-ylcyclopentadienyl)titanium dichloride
[1,3-bis(trimethylsilyl)cyclopentadienyl](3,4-benzofluorenyl)niobium dichloride
bis(cyclopentadienyl)titanium dibromide
dimethylsilanediylbis(indenyl)titanium dibromide
dimethylsilanediylbis(tetrahydroindenyl)hafnium dichloride
dimethylsilanediyl(cyclopentadienyl)(indenyl)titanium dichloride
dimethylsilanediylbis(2-methylindenyl)hafnium dichloride
dimethylsilanediylbis(2-ethylindenyl)scandium chloride
dimethylsilanediylbis(2-butyl-4,5-benzoindenyl)niobium diiodide
dimethylsilanediylbis(2-ethyl-4,5-benzoindenyl)titanium diiodide
dimethylsilanediylbis(4,5-dihydro-8-methyl-7H-cyclopent[e]acenaphthylen-7-ylidene]titanium dichloride
dimethylsilanediyl(2-methyl-4,5-benzoindenyl)(2-methyl-4-phenylindenyl)titanium dichloride
dimethylsilanediyl(2-ethyl-4,5-benzoindenyl)(2-methyl-4-phenylindenyl)hafnium dibromide
dimethylsilanediyl(2-methyl-4,5-benzoindenyl)(2-ethyl-4-phenylindenyl)scandium chloride
dimethylsilanediyl(2-ethyl-4,5-benzoindenyl)(2-ethyl-4-naphthylindenyl)titanium dibromide
dimethylsilanediyl(2-methylindenyl)(4-phenylindenyl)hafnium dibromide
dimethylsilanediylbis(2-methyl-4-phenylindenyl)niobium dimethoxide
dimethylsilanediylbis(2-ethyl-4-phenylindenyl)vanadium dimethoxide
dimethylsilanediylbis(2-methyl-4,6-diisopropylindenyl)hafnium dichloride
dimethylsilanediylbis(2-ethyl-4,6-diisopropylindenyl)vanadium dichloride
dimethylsilanediylbis(2-methyl-4-naphthylindenyl)hafnium bromide chloride
dimethylsilanediylbis(2-ethyl-4-naphthylindenyl)titanium dichloride
methylphenylsilanediylbis(indenyl)titanium dichloride
methylphenylsilanediyl(cyclopentadienyl)(indenyl)hafnium dichloride
methylphenylsilanediylbis(tetrahydroindenyl)hafnium dichloride
methylphenylsilanediylbis(2-methylindenyl)titanium dichloride
methylphenylsilanediylbis(2-ethylindenyl)hafnium dichloride
methylphenylsilanediylbis(2-methyl-4,5-benzoindenyl)hafnium dichloride
methylphenylsilanediylbis(2-ethyl-4,5-benzoindenyl)vanadium diiodide
methylphenylsilanediylbis(4,5-dihydro-8-methyl-7H-cyclopent[acenaphthylen-7-ylidene)titanium diiodide
methylphenylsilanediyl(2-methyl-4,5-benzoindenyl)(2-methyl-4-phenylindenyl)titanium bromide chloride
methylphenylsilanediyl(2-ethyl-4,5-benzoindenyl)(2-methyl-4-phenylindenyl)titanium dibromide
methylphenylsilanediyl(2-methyl-4,5-benzoindenyl)(2-ethyl-4-phenylindenyl)hafnium dibromide
methylphenylsilanediyl(2-ethyl-4,5-benzoindenyl )(2-ethyl-4-naphthylindenyl)hafnium dibromide
methylphenylsilanediyl(2-methylindenyl)(4-phenylindenyl)titanium dichloride
methylphenylsilanediylbis(2-methyl4-phenylindenyl)hafnium dimethoxide
methylphenylsilanediylbis(2-ethyl-4-phenylindenyl)vanadium dichloride
methylphenylsilanediylbis(2-ethyl-4,6-diisopropylindenyl)titanium dichloride
methylphenylsilanediylbis(2-ethyl-4,6-diisopropylindenyl)hafnium dichloride
methylphenylsilanediylbis(2-methyl-4-naphthylindenyl)hafnium dichloride
methylphenylsilanediylbis(2-ethyl-4-naphthyl indenyl)titanium dichloride
diphenylsilanediylbis(indenyl)titanium dichloride
diphenylsilanediylbis(2-methylindenyl)hafnium dichloride
diphenylsilanediylbis(2-ethylindenyl)titanium dichloride
diphenylsilanediyl(cyclopentadienyl)(indenyl)hafnium dichloride
diphenylsilanediylbis(2-methyl-4,5-benzoindenyl)titanium dichloride
diphenylsilanediylbis(2-ethyl-4,5-benzoindenyl)hafnium dichloride
diphenylsilanediyl(2-methyl-4,5-benzoindenyl)(2-methyl-4-phenylindenyl)hafnium dichloride
diphenylsilanediyl(2-ethyl-4,5-benzoindenyl)(2-methyl-4-phenylindenyl)titanium diiodide
diphenylsilanediyl(2-methyl-4,5-benzoindenyl)(2-ethyl-4-phenyl indenyl)hafnium diiodide
diphenylsilanediyl(2-ethyl-4,5-benzoindenyl)(2-ethyl-4-naphthylindenyl)titanium dibromide diphenylsilanediyl(2-methylindenyl)(4-phenylindenyl) titanium dibromide
diphenylsilanediylbis(2-methyl-4-phenylindenyl)titanium dibromide
diphenylsilanediylbis(2-ethyl-4-phenylindenyl)hafnium dibromide
diphenylsilanediylbis(2-methyl-4,6-diisopropylindenyl) hafnium dichloride
diphenylsilanediylbis(2-ethyl-4,6-diisopropylindenyl) hafnium dibromide
diphenylsilanediylbis(2-methyl-4-naphthylindenyl)hafnium dichloride
diphenylsilanediylbis(2-ethyl-4-naphthylindenyl)titanium dichloride
1-silacyclopentane-1,1-bis(indenyl)hafnium dimethoxide
1-silacyclopentane-1,1-bis(2-methylindenyl)hafnium dibromide
1-silacyclopentane-1,1-bis(2-ethylindenyl)hafnium dimethoxide
1-silacyclopentane-1,1 -bis(2-methyl-4,5-benzoindenyl) titanium dimethoxide
1-silacyclopentane-1-bis(2-ethyl-4,5-benzoindenyl)hafnium dichloride
1-silacyclopentane-1-(2-methyl 4,5-benzoindenyl)-1-(2-methyl-4-phenylindenyl)scandium chloride
1-silacyclopentane-1-(2-ethyl-4,5-benzoindenyl)-1 -(2-methyl-4-phenylindenyl)hafnium dichloride
1-silacyclopentane-1-(2-methyl-4,5-benzoindenyl)-1-(2-ethyl4-phenylindenyl)titanium dichloride
1-silacyclopentane-1-(2-ethyl-4,5-benzoindenyl)-1 -(2-ethyl-4-naphthylindenyl)hafnium dichloride
1-silacyclopentane-1-(2-methylindenyl)-1-(4-phenylindenyl)hafnium dichloride
1-silacyclopentane-1,1-bis(2-methyl-4-phenylindenyl) hafnium dichloride
1-silacyclopentane-1,1 -bis(2-ethyl-4-phenylindenyl) titanium bromide chloride
1-silacyclopentane-1,1 -bis(2-methyl-4,6-diisopropylindenyl)titanium dibromide
1-silacyclopentane-1,1-bis(2-ethyl-4,6-diisopropylindenyl) titanium dichloride
1-silacyclopentane-1,1-bis(2-methyl-4-naphthylindenyl) scandium chloride
1-silacyclopentane-1,1 -bis(2-ethyl-4-naphthylindenyl) hafnium dichloride
bis(cyclopentadienyl)titanium dichloride
ethylene-1,2-bis(indenyl)scandium chloride
ethylene-1,2-bis(tetrahydroindenyl)titanium dichloride
ethylene-1-cyclopentadienyl-2-(1-indenyl)hafnium dichloride
ethylene-1-cyclopentadienyl-2-(2-indenyl)titanium bromide chloride
ethylene-1-cyclopentadienyl-2-(2-methyl-1-indenyl) hafnium dimethoxide
ethylene-1,2-bis(2-methylindenyl)hafnium diiodide
ethylene-1,2-bis(2-ethylindenyl)hafnium diiodide
ethylene-1,2-bis(2-methyl4,5-benzoindenyl)hafnium dichloride
ethylene-1,2-bis(2-ethyl4,5-benzoindenyl)titanium dichloride
ethylene-1,2-bis(4,5-dihydro-8-methyl-7H-cyclopent [acenaphthylen-7-ylidene]titanium dibromide
ethylene-1-(2-methyl4,5-benzoindenyl)-2-(2-methyl-4-phenylindenyl)titanium dibromide
ethylene-1-(2-ethyl-4,5-benzoindenyl)-2-(2-methyl-4-phenylindenyl)titanium dichloride
ethylene-1-(2-methyl-4,5-benzoindenyl )-2-(2-ethyl-4-phenylindenyl)scandium chloride
ethylene-1-(2-ethyl-4,5-benzoindenyl)-2-(2-ethyl-4-naphthylindenyl)hafnium dichloride
ethylene-1-(2-methylindenyl)-2-(4-phenylindenyl)titanium dichloride
ethylene-1,2-bis(2-methyl-4-phenylindenyl)hafnium dichloride
ethylene-1,2-bis(2-ethyl-4-phenylindenyl)hafnium dichloride
ethylene-1,2-bis(2-methyl-4,6-diisopropylindenyl)hafnium dichloride
ethylene-1,2-bis(2-ethyl4,6-diisopropylindenyl)titanium dichloride
ethylene-1,2-bis(2-methyl-4-naphthylindenyl)titanium dichloride
ethylene-1,2-bis(2-ethyl4-naphthylindenyl)hafnium dichloride
propylene-2,2-bis(indenyl)hafnium dichloride
propylene-2-cyclopentadienyl-2-(i-indenyl)titanium dichloride
propylene-2-cyclopentadienyl-2-(4-phenyl-1-indenyl) titanium dichloride
propylene-2-cyclopentadienyl-2-(9-fluorenyl)hafnium dichloride
propylene-2-cyclopentadienyl-2-(2,7-dimethoxy-9-fluorenyl)hafnium dichloride
propylene-2-cyclopentadienyl-2-(2,7-di-tert-butyl-9-fluorenyl)hafnium diiodide
propylene-2-cyclopentadienyl-2-(2,7-dibromo-9-fluorenyl) titanium diiodide
propylene-2-cyclopentadienyl-2-(2,7-diphenyl-9-fluorenyl) hafnium dichloride
propylene-2-cyclopentadienyl-2-(2,7-dimethyl-9-fluorenyl) titanium dichloride
propylene-2-(3-methylcyclopentadienyl)-2-(2,7-dibutyl-9-fluorenyl)hafnium difluoride
propylene-2-(3-tert-butylcyclopentadienyl)-2-(2,7-dibutyl-9-fluorenyl)titanium difluoride
propylene-2-(3-trimethylsilylcyclopentadienyl)-2-(3,6-di-tert-butyl-9-fluorenyl)titanium difluoride
propylene-2-cyclopentadienyl-2-[2,7-bis(3-buten-1-yl)-9-fluorenyl]hafnium diiodide
propylene-2-cyclopentadienyl-2-(3-tert-butyl-9-fluorenyl) titanium dibromide
propylene-2,2-bis(tetrahydroindenyl)hafnium dibromide
propylene-2,2-bis(2-methylindenyl)hafnium dichloride
propylene-2,2-bis(2-ethylindenyl)titanium dichloride
propylene-2,2-bis(2-methyl-4,5-benzoindenyl)titanium dichloride
propylene-2,2-bis(2-ethyl-4,5-benzoindenyl)hafnium dichloride
propylene-2,2-bis(4,5-dihydro-8-methyl-7H-cyclopent[e] acenaphthylen-7-ylidene]hafnium dichloride
propylene-2-(2-methyl-4,5-benzoindenyl)-2-(2-methyl-4-phenylindenyl)hafnium dichloride
propylene-2-(2-ethyl-4,5-benzoindenyl)-2-(2-methyl-4-phenylindenyl)titanium dichloride
propylene-2-(2-methyl-4,5-benzoindenyl )-2-(2-ethyl-4-phenyl indenyl)hafnium dichloride
propylene-2-(2-ethyl-4,5-benzoindenyl )-2-(2-ethyl-4-naphthylindenyl)titanium dichloride
propylene-2-(2-methylindenyl)-2-(4-phenylindenyl) hafnium dichloride
propylene-2,2-bis(2-methyl-4-phenylindenyl)titanium diiodide
propylene-2,2-bis(2-ethyl-4-phenylindenyl )hafnium diiodide
propylene-2,2-bis(2-methyl-4,6-diisopropylindenyl) titanium diiodide propylene-2,2-bis(2-ethyl-4,6-diisopropylindenyl)hafnium dichloride
propylene-2,2-bis(2-methyl-4-naphthylindenyl)titanium dichloride
propylene-2,2-bis(2-ethyl-4-naphthylindenyl)titanium dichloride
1,6-bis[methylsilylbis(2-methyl-4-phenylindenyl)hafnium dichloride]hexane
1,6-bis[methylsilylbis(2-methyl-4,5-benzoindenyl)titanium dichloride]hexane
1,6-bis[methylsilylbis(2-ethyl-4-phenylindenyl)hafnium dichloride]hexane
1,6-bis[methylsilylbis(2-methyl-4-naphthylindenyl) titanium dichloride]hexane
1,6-bis[methylsilylbis(2-methyl4,6-diisopropylindenyl) hafnium dichloride]hexane
1,6-bis[methylsilyl(2-methyl-4-phenylindenyl)(4,5-benzoindenyl)titanium dichloride]hexane
1-[methylsilylbis(tetrahydroindenyl)hafnium dichloride]-6-[ethylstannyl(cyclopentadienyl)(fluorenyl)titanium dichloride]hexane
1,6-disila-1,6,6-tetramethyl-1,6-bis[methylsilylbis(2-methyl4-phenylindenyl)hafnium diiodide]hexane
1,4-disila-1,4-bis[methylsilylbis(2-methyl-4-phenylindenyl) hafnium diiodide]cyclohexane
[1,4-bis(1-indenyl)-1,1,4,4-tetramethyl-1,4-disilabutane]bis (pentamethylcyclopentadienylhafnium diiodide)
[1,4-bis(9-fluorenyl)-1,1,4,4-tetramethyl-1,4-disilabutane] bis(cyclopentadienylhafnium dichloride)
[1,4-bis(1-indenyl)-1,1,4,4-tetramethyl-1,4-disilabutane]bis (cyclopentadienyltitanium dichloride)
[1-(1-indenyl)-6-(2-phenyl-1-indenyl)-1,6,6-tetraethyl-1,6-disila-4-oxahexane]bis(tert-butylcyclopentadienyltitanium dibromide)
[1,10-bis(2,3-dimethyl-1-indenyl)-1,1,10,10-tetramethyl-1,10-digermadecane]bis(2-methyl-4-phenylindenylhafnium dibromide)
(1-methyl-3-tert-butylcyclopentadienyl)(1-phenyl-4-methoxy-7-chlorofluorenyl)titanium dichloride
(4,7-dichloroindenyl)(3,6-dimesitylfluorenyl)titanium dichloride
bis(2,7-di-tert-butyl-9-cyclohexylfluorenyl)hafnium diiodide
(2,7-dimesitylfluorenyl)[2,7-bis(1-naphthyl)fluorenyl] hafnium dichloride
dimethylsilylbis(fluorenyl)titanium dichloride
dibutylstannylbis(2-methylfluorenyl)hafnium dichloride
1,1,2,2-tetraethyldisilanediyl(2-methylindenyl)(4-phenylfluorenyl)titanium dichloride
propylene-1-(2-indenyl)-2-(9-fluorenyl)hafnium dichloride
1,1-dimethyl-1-silaethylenebis(fluorenyl)titanium dichloride
[4-(cyclopentadienyl)-4,7,7-trimethyl(tetrahydroindenyl)] titanium difluoride
[4-(cyclopentadienyl)4,7-dimethyl-7-phenyl(5,6-dimethyltetrahydroindenyl)]hafnium difluoride
[4-(cyclopentadienyl)-4,7-dimethyl-7-(1-naphthyl)(7-phenyltetrahydroindenyl)]titanium dichloride
[4-(cyclopentadienyl)-4,7-dimethyl-7-butyl(6,6-diethyltetrahydroindenyl)]hafnium dichloride
[4-(3-tert-butylcyclopentadienyl)-4,7,7-trimethyl (tetrahydroindenyl)]hafnium dibromide
[4-(1-indenyl)-4,7,7-trimethyl(tetrahydroindenyl)]titanium dibromide For the purposes of the present invention, the term "polar extractant" includes polar solvents, mixtures of various polar solvents or mixtures of one or more polar solvents with one or more nonpolar solvents. The polar extractant contains from 5 to 100% by volume, preferably from 25 to 100% by volume, particularly preferably from 60 to 100% by volume, of one or more polar solvents, in each case based on the total volume of the polar extractant. Polar extractants which can be used are, for example, protic, aprotic, organic and inorganic solvents and also mixtures thereof.

Examples of polar solvents are water, ammonia or organic solvents. Examples of organic solvents are alcohols such as methanol, ethanol, 1-propanol, 2-propanol, 1-butanol, 2-butanol, isobutanol, tert-butanol, 1-pentanol, 2-pentanol, 3-pentanol, amyl alcohol, isoamyl alcohol, 1-hexanol, 2-hexanol, 3-hexanol, 2-methyl-2-pentanol, 2-methyl-3-pentanol, 3-methyl-3-pentanol, 1-heptanol, 2-heptanol, 3-heptanol, 4-heptanol, 2-methyl-2-hexanol, 3-methyl-3-hexanol, 4-methyl-4-hexanol, 2-methyl4-hexanol, 4-methyl-2-hexanol, 2-ethylhexanol, benzyl alcohol, phenol, resorcinol, 1-phenylethanol, 2-phenylethanol, 1-phenyl-2-butanol, 3-phenyl-1-butanol, 1,2-propanediol, 1,3-propanediol, 1,2-butanediol, 1,3-butanediol, 1,4-butanediol, ethylene glycol or glycerol, amines such as ethanolamine, propanolamine, methylamine, dimethylamine, trimethylamine, ethylamine, diethylamine, triethylamine, methylethylamine, methylbutylamine, propylamine, dipropylamine, tripropylamine, diisopropylamine, triisopropylamine, tert-butylamine, 1,2-ethylenediamine, N,N,N',N'-tetramethyl-1,2-ethylenediamine, Di(n-butyl)amine, tributylamine, aniline, N-methylaniline, N,N-dimethylaniline, toluidine or N,N-dimethyltoluidine, aldehydes such as acetaldehyde, butyraldehyde, hexanal or propionaldehyde, ketones such as butanone, acetone, methyl propyl ketone or diethyl ketone, carboxylic acids such as formic acid, acetic acid, propionic acid, butyric acid, isobutyric acid, pentanoic acid or hexanoic acid, carboxylic esters such as methyl formate, ethyl formate, propyl formate, butyl formate, methyl acetate, ethyl acetate, propyl acetate, butyl acetate, methyl propionate or butyl propionate, ethers such as dimethyl ether, diethyl ether, methyl ethyl ether, dibutyl ether, diisopropyl ether, dioxane, trioxane, tetrahydrofuran or dimethoxyethane, hetero aromatics such as furan, pyrrole, pyridine or thiophene, carboxamides such as formamide, dimethylformamide, diethylformamide, dimethylacetamide, diethylacetamide or N-methylpyrrolidone, nitriles such as acetonitrile, propionitrile or butyronitrile, halo aromatics such as chlorobenzene, 1,2-dichlorobenzene, 1,3-dichlorobenzene or bromobenzene, alkyl halides such as ethyl bromide, ethyl chloride, ethyl fluoride, butyl bromide, butyl chloride, methyl chloride or dichloromethane and nitro compounds such as nitromethane, nitroethane, 1-nitropropane, 2-nitropropane, 1-nitrobutane, 2-nitrobutane, nitrobenzene, 2-nitrotoluene or 3-nitrotoluene.

Examples of nonpolar solvents are alkanes such as propane, butane, isobutane, pentane, 2-methylbutane, neopentane, cyclopentane, hexane, 2-methylpentane, 3-methylpentane, heptane, 2-methylhexane, 3-methylhexane, cyclohexane, octane, isooctane, nonane, isononane or decane and aromatic hydrocarbons such as benzene, toluene or xylene.

Preferred polar extractants are methanol, ethanol, 2-butanol, isobutanol, acetone, dichloromethane, tetrahydrofuran, dioxane, dimethoxyethane, methanol/water, ethanol/water, 2-butanol/water, isobutanol/water, pentane/methanol, pentane/ethanol, hexane/2-butanol, heptane/isobutanol, octane/acetone or heptane/toluene/isobutanol. The total proportion by volume of all polar solvents is here from 5 to 100%, preferably from 25 to 100%, particularly preferably from 60 to 100%. Particularly preferred polar extractants are ethanol, isobutanol, acetone, tetrahydrofuran, dioxane, dimethoxyethane, heptane/isobutanol, heptane/toluene/isobutanol.

In the process of the invention, one or more inorganic by-products (e.g. inorganic salts or covalent metal halides) can go into solution in the polar extractant. The desired metallocene remains as a solid and can be isolated, for example, by filtration, centrifugation or decantation. This enables the undesired inorganic by-products to be removed under mild conditions from the desired metallocene in a short time using relatively small amounts of extractant.

In the process of the invention, it is also possible for one or more organometallic by-products (e.g. undesired isomers of the desired metallocene) to go into solution in the polar extractant (possibly with decomposition). The desired metallocene remains as a solid and can be isolated, for example, by filtration, centrifugation or decantation. This enables the undesired organometallic by-products to be removed under mild conditions from the desired metallocene in a short time using relatively small amounts of extractant.

The process of the invention gives a high space-time yield. In addition, the process of the invention enables the separation times (e.g. filtration times) to be greatly reduced so that even large amounts of metallocene can be purified or upgraded simply, quickly and inexpensively. The process of the invention is particularly suitable for separating metallocene isomers, e.g. in the purification of chiral metallocenes for separating the meso form from the racemic form.

The process of the invention can be carried out, for example, by suspending the crude product formed in the metallocene synthesis, comprising at least one metallocene and at least one organometallic and/or inorganic by-product, in a polar extractant at temperatures between −50° and +150° C., preferably between −50° and +100° C., particularly preferably between −10° and +60° C., very particularly preferably between 0° and +40° C., and mixing vigorously. Alternatively, a crude product suspension formed in the metallocene synthesis, comprising at least one metallocene and at least one inorganic by-product, can also be admixed directly with a polar extractant at temperatures between −50° and +150° C., preferably between −50° and +100° C., particularly preferably between −10° and +60° C., very particularly preferably between 0° and +40° C. The polar extractant comprises at least one polar solvent or a mixture of various polar solvents or a mixture of one or more polar solvents with one or more nonpolar solvents. The crude product can be treated directly with the polar extractant. If a mixture of polar and, where appropriate, nonpolar solvents is to be used, the individual solvents can also be brought into contact with the crude product successively, for example first the nonpolar solvents and then the polar solvents or vice versa. During the contact time with the polar extractant, which can be between 1 minute and 3 days, preferably between 5 minutes and 24 hours, particularly preferably between 10 minutes and 6 hours, the organometallic and/or inorganic by-products go into solution. The remaining solid is subsequently separated from the solution, e.g. by filtration, centrifugation or decantation. The organometallic by-products (e.g. isomers of the desired metallocene, ligand residues, ligand fragments or oligomeric by-products) and/or inorganic by-products are thus separated off. The product obtained as a solid comprises the desired metallocene in purified or upgraded form, preferably in excess. The process of the invention generally leads to a reduction in the concentration of the inorganic by-products in the mixture treated with the polar extractant to below 5% by weight, based on the total amount of the solid product. Concentrations of less than 0.1% by weight of inorganic by-products can also be achieved, in particular by repeating the treatment of the mixture with a polar extractant one or more times.

The process of the invention generally leads to a reduction in the concentration of the organometallic by-products in the mixture treated with the polar extractant to below 10% by weight, based on the total amount of the solid product.

Concentrations of less than 0.5% by weight of organometallic by-products can also be achieved, in particular by repeating the treatment of the mixture with a polar extractant one or more times.

The following examples illustrate the invention but do not limit it in any way. The rac/meso ratio was determined by $^1$H-NMR spectroscopy (signals at 2.8 ppm).

EXAMPLE 1

A suspension comprising 5.0 g of dimethylsilanediylbis(2-methylindenyl)zirconium dichloride (rac/meso mixture in a ratio of 1/1), 30 ml of heptane and 30 ml of acetone is stirred for 30 minutes at 25° C. and subsequently filtered through a G3 frit. The residue is washed with 10 ml of heptane and freed of solvent under reduced pressure. The yield of dimethylsilanediylbis(2-methylindenyl)zirconium dichloride is 1.75 g (35%) (rac/meso ratio =11/1).

EXAMPLE 2

A suspension comprising 5.0 g of dimethylsilanediylbis(2-methylindenyl)zirconium dichloride (rac/meso mixture in a ratio of 1/1) and 20 ml of isobutanol is stirred for 30 minutes at 25° C. and subsequently filtered through a G3 frit. The residue is washed with 10 ml of heptane and freed of solvent under reduced pressure. The yield of dimethylsilanediylbis(2-methylindenyl)zirconium dichloride is 1.9 g (38%) (rac/meso ratio=11/1).

EXAMPLE 3

A suspension comprising 2.5 g of dimethylsilanediylbis(2-methylindenyl)zirconium dichloride and 1.9 g of lithium chloride is stirred in 50 ml of heptane and 35 ml of isobutanol for 30 minutes at 0° C. and subsequently filtered through a G3 frit. The residue is freed of solvent under reduced pressure. The yield of dimethylsilanediylbis(2-methylindenyl)zirconium dichloride is 2.4 g (lithium chloride content: 2.2%).

EXAMPLE 4

A suspension comprising 35 g of dimethylsilanediylbis(2-methylindenyl)zirconium dichloride and 23.3 g of lithium chloride is stirred in 350 ml of heptane and 375 ml of isobutanol for 30 minutes at 0° C. and subsequently filtered through a G3 frit. The 30 residue is freed of solvent under reduced pressure. The yield of dimethylsilanediylbis(2-methylindenyl)zirconium dichloride is 25.4 g (lithium chloride content: 0.8%).

We claim:

1. A process for reducing the concentration of organometallic byproducts or inorganic by-products or both organometallic and inorganic products in product mixtures formed in the synthesis of metallocene products, which comprises treating a mixture comprising one or more metallocene products and one or more organometallic byproducts or one or more inorganic byproducts or both said byproducts with a polar extractant composition comprising a polar organic solvent, to obtain the desired product with reduced concentration of byproducts, said polar organic solvent being an alcohol, an amine, an aldehyde, a ketone, a carboxylic acid, a carboxylic acid ester, an ether, a heteroaromatic compound, a nitrile, a haloaromatic compound, a nitro compound, or a combination thereof.

2. The process as claimed in claim 1, wherein the mixture is a crude product formed in the synthesis of at least one metallocene product.

3. The process as claimed in claim 1, wherein the polar extractant composition contains from 5 to 100% by volume of one or more polar solvents, based on the total volume of the polar extractant composition.

4. The process as claimed in claim 1, wherein the concentration of the inorganic by-products is reduced to less than 5% by weight, based on the total amount of said desired product obtained in the process.

5. The process as claimed in claim 1, wherein the inorganic by-products are inorganic salts or covalent metal halides or mixtures thereof.

6. The process as claimed in claim 1, wherein the concentration of the organometallic by-products is reduced to less than 10% by weight, based on the total amount of said desired product obtained in the process.

7. The process as claimed in claim 1, wherein the mixture comprises the racemic form and the meso form of a metallocene.

8. The process as claimed in claim 1, wherein said treating of the mixture provides a solution containing said byproducts, wherein said desired product is obtained as a solid comprising a desired metallocene in purified or upgraded form, and wherein said desired metallocene in purified or upgraded from is isolated from the thus-treated mixture.

9. The process as claimed in claim 1, wherein said polar extractant composition comprises a said polar organic solvent, alone or in combination with a nonpolar organic solvent, an inorganic solvent, or a combination of a nonpolar organic solvent and an inorganic solvent.

10. The process as claimed in claim 9, wherein said polar extractant composition comprises a said polar organic solvent and a nonpolar organic solvent or inorganic solvent.

11. The process as claimed in claim 9, wherein said polar extractant composition comprises a said organic polar solvent and at least one further solvent which further solvent or solvents is or are water, an alkane, or an aromatic compound.

12. A process for reducing the concentration of organometallic byproducts or inorganic byproducts or both organometallic and inorganic products in a product mixture formed in the synthesis of a metallocene product, which comprises:

carrying out a metallocene synthesis to obtain a crude product mixture containing at least one metallocene product contaminated with at least one of said byproducts, contacting said crude product mixture with a polar extractant composition for a contact time ranging from 1 minute to 3 days, until said byproduct or byproducts go into solution and a solid is formed in the thus-treated product mixture, said solid comprising a desired metallocene product, and separating off said solid to obtain a desired metallocene in purified or upgraded form, said polar extractant composition containing a polar organic solvent, said polar organic solvent being an alcohol, an amine, an aldehyde, a ketone, a carboxylic acid, a carboxylic acid ester, an ether, a heteroaromatic compound, a nitrile, a haloaromatic compound, a nitro compound, or a combination thereof.

* * * * *